(12) United States Patent
Sotos et al.

(10) Patent No.: US 7,841,987 B2
(45) Date of Patent: Nov. 30, 2010

(54) SYSTEM AND METHOD FOR VISUALIZING SLEEP-RELATED INFORMATION

(75) Inventors: John G. Sotos, Palo Alto, CA (US); John L. Branscum, Jr., Belmont, CA (US)

(73) Assignee: Apneos Corporation, Belmont, CA (US)

( * ) Notice: Subject to any disclaimer, the term of this patent is extended or adjusted under 35 U.S.C. 154(b) by 36 days.

(21) Appl. No.: 11/095,154

(22) Filed: Mar. 31, 2005

(65) Prior Publication Data

US 2006/0063981 A1    Mar. 23, 2006

Related U.S. Application Data

(60) Provisional application No. 60/557,735, filed on Mar. 30, 2004, provisional application No. 60/610,888, filed on Sep. 18, 2004.

(51) Int. Cl.
*A61B 5/08* (2006.01)
*A61B 7/00* (2006.01)

(52) U.S. Cl. ................................. 600/529; 600/586

(58) Field of Classification Search .......... 600/586, 600/529
See application file for complete search history.

(56) References Cited

U.S. PATENT DOCUMENTS

| | | | |
|---|---|---|---|
| 4,732,159 A * | 3/1988 | Kraman | 600/534 |
| 4,982,738 A * | 1/1991 | Griebel | 600/483 |
| 5,275,159 A | 1/1994 | Griebel | |
| 5,520,176 A | 5/1996 | Cohen | |
| 5,797,852 A | 8/1998 | Karakasoglu | |
| 6,120,441 A * | 9/2000 | Griebel | 600/300 |
| 6,168,568 B1 * | 1/2001 | Gavriely | 600/529 |
| 6,171,258 B1 | 1/2001 | Karakasoglu | |
| 6,213,955 B1 | 4/2001 | Karakasoglu | |
| 6,261,238 B1 | 7/2001 | Gavriely | |
| 6,283,923 B1 * | 9/2001 | Finkelstein et al. | 600/532 |
| 6,290,654 B1 | 9/2001 | Karakasoglu | |
| 6,306,088 B1 | 10/2001 | Krausman | |
| 6,319,205 B1 | 11/2001 | Goor | |
| 6,322,515 B1 | 11/2001 | Goor | |
| 6,666,830 B1 | 12/2003 | Lehman | |
| 6,811,538 B2 | 11/2004 | Westbrook | |

OTHER PUBLICATIONS

U.S. Appl. No. 11/094,911, Sotos.

* cited by examiner

*Primary Examiner*—Patricia C Mallari

(57) ABSTRACT

A method for improved visualization of information related to the physiology of a sleeping patient is disclosed. Physiological information from the patient is obtained by a device, converted to digital format, and transformed into physiological data of two or more types. Physiological data of two or more types are combined into a compact graphical display representing data from all physiological data types.

12 Claims, 11 Drawing Sheets

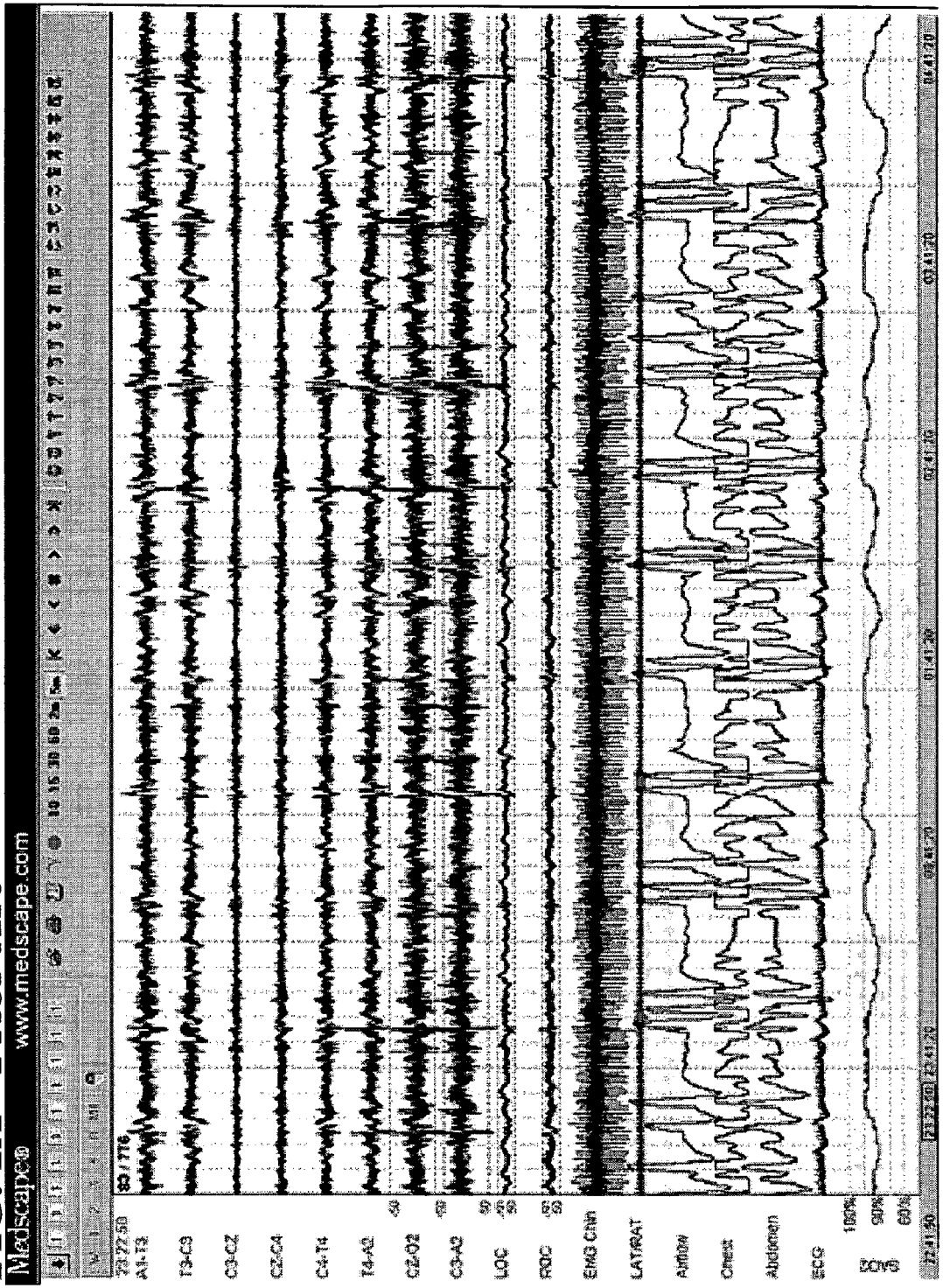
FIG. 1A - Prior Art

FIG. 1B - Prior Art
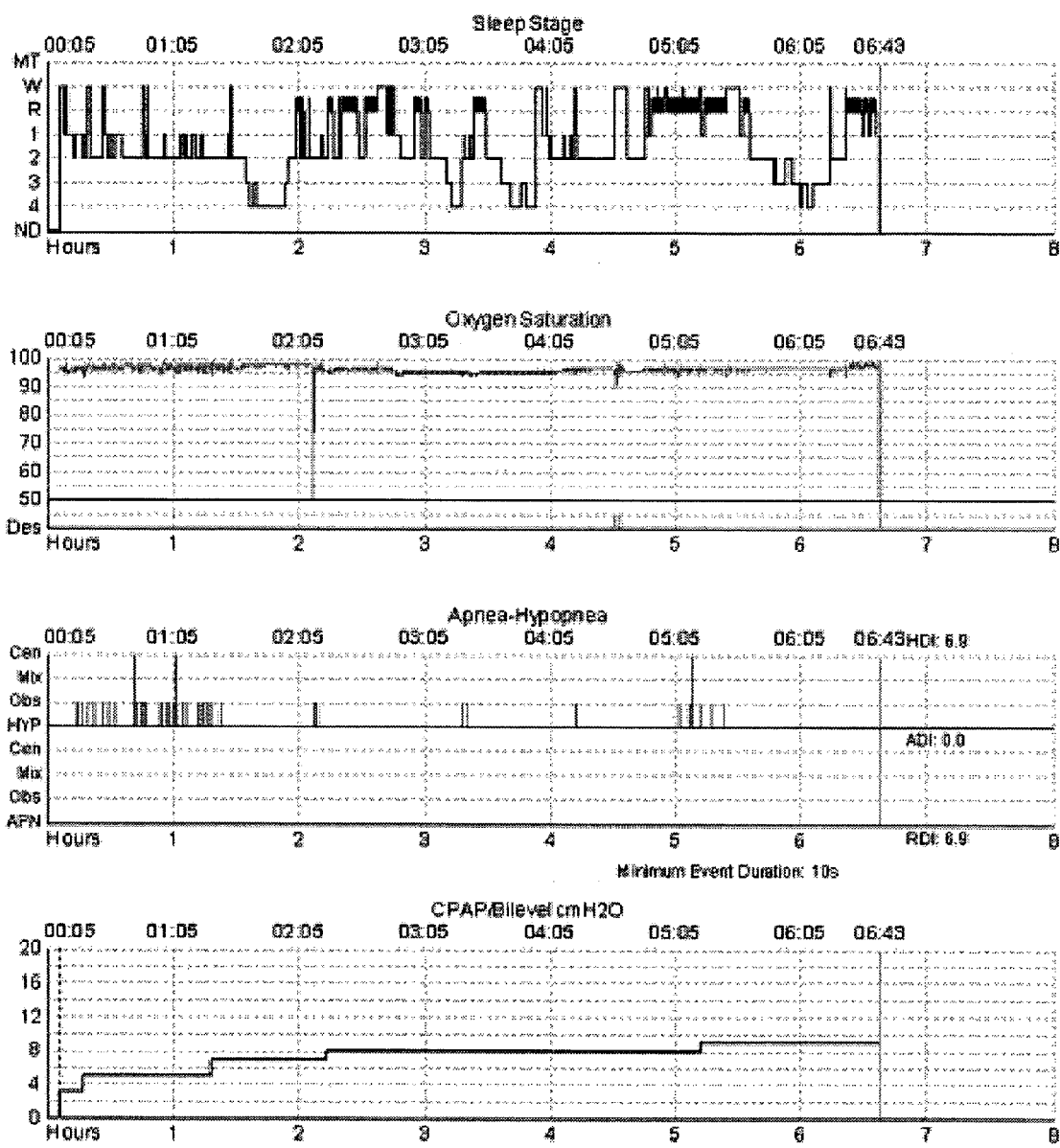

FIG. 2 - Prior Art
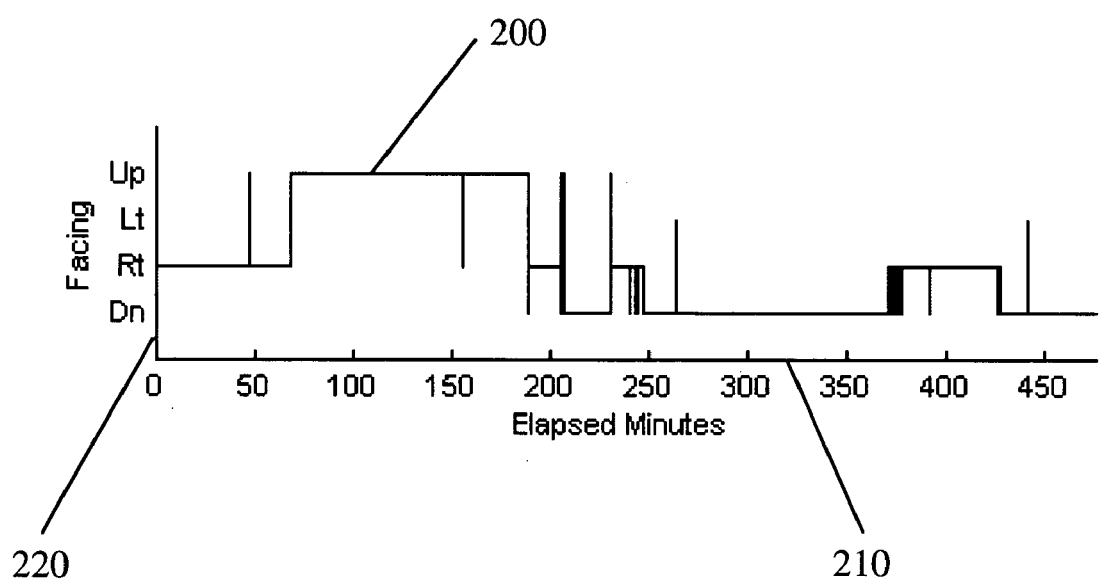

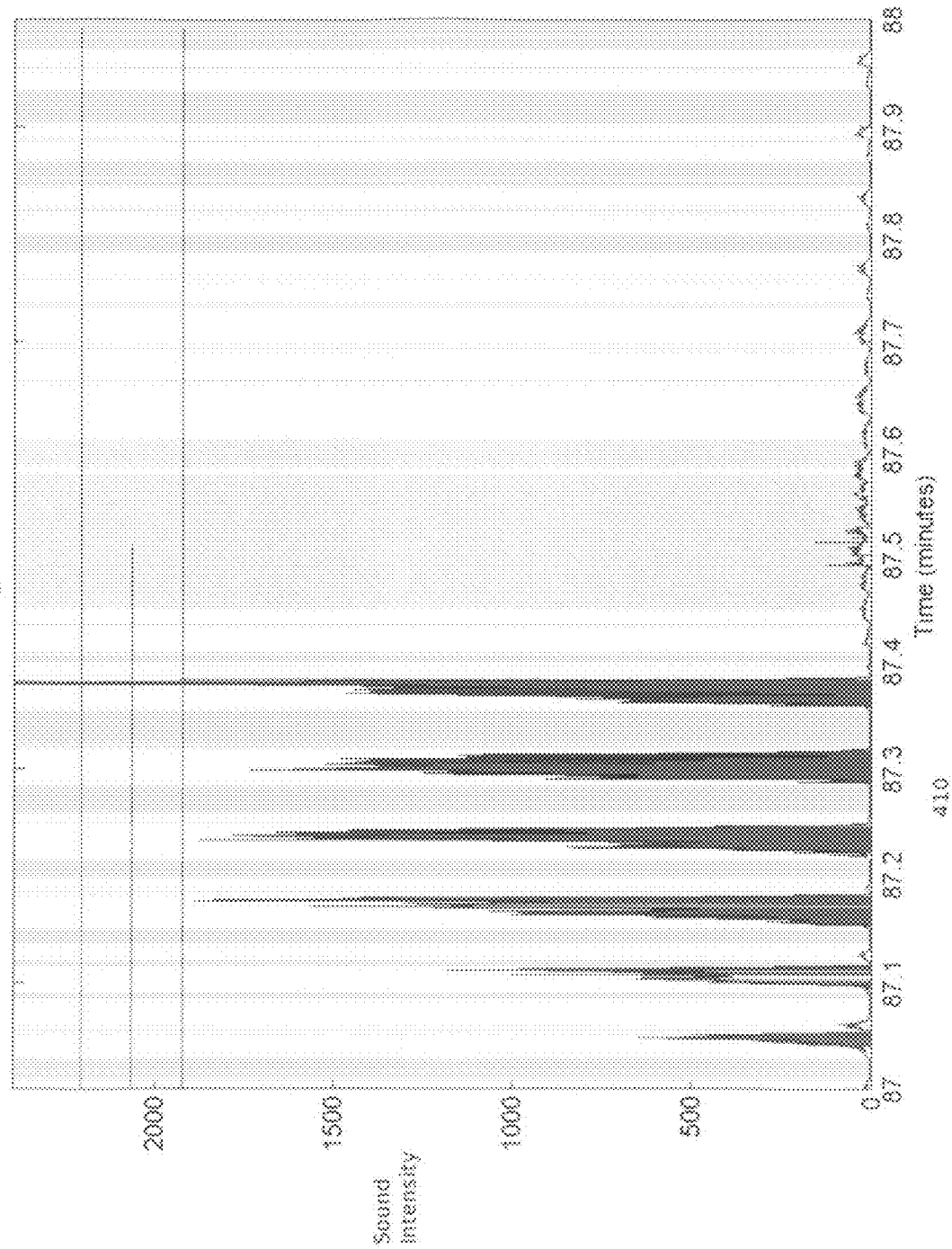

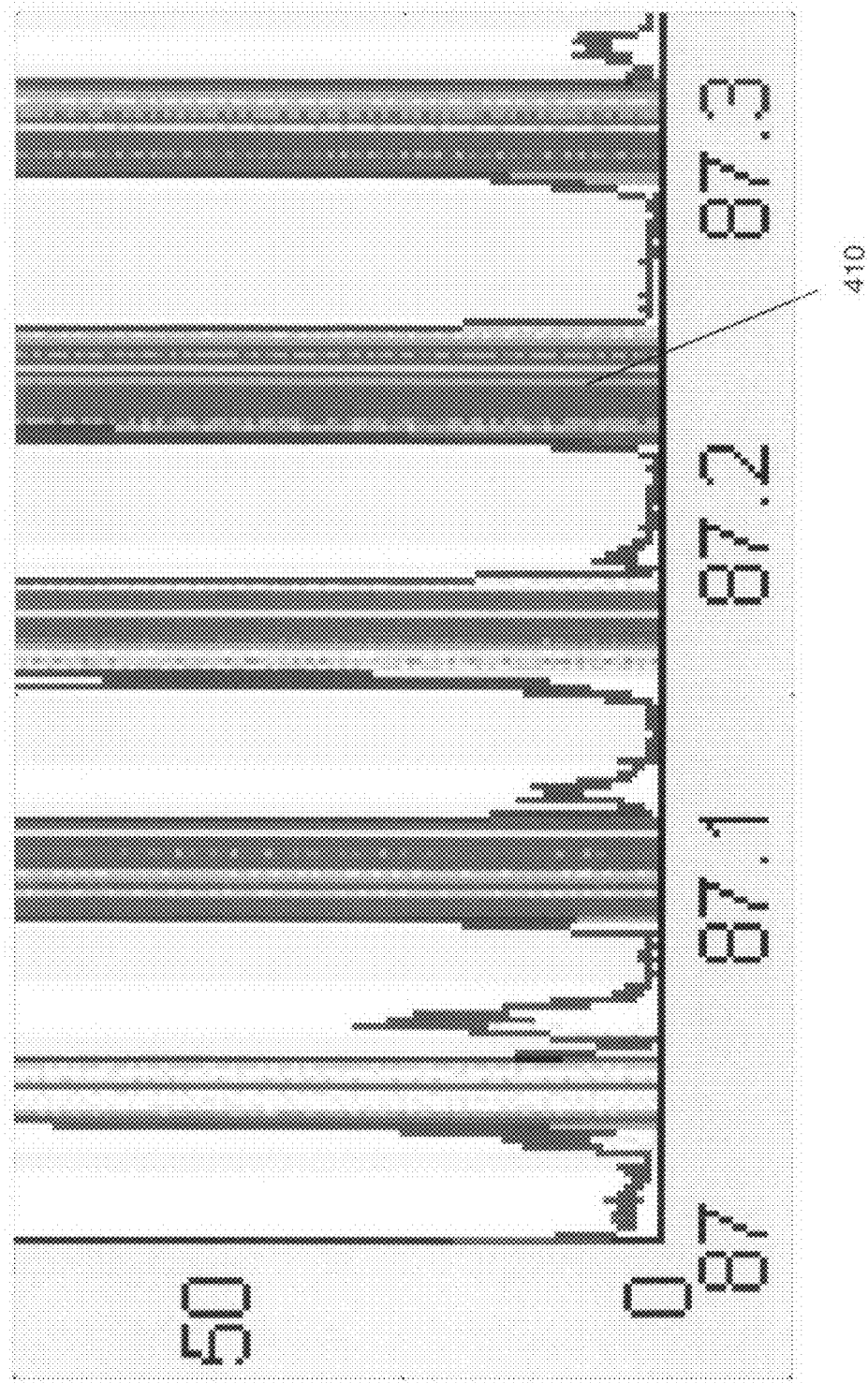

SYSTEM AND METHOD FOR VISUALIZING SLEEP-RELATED INFORMATION

CROSS-REFERENCES TO RELATED APPLICATIONS

This application claims priority to U.S. Provisional Patent No. 60/557,735 filed Mar. 30, 2004, commonly assigned, and hereby incorporated by reference for all purposes.

This application claims priority to U.S. Provisional Patent No. 60/610,888 filed Sep. 18, 2004, commonly assigned, and hereby incorporated by reference for all purposes.

BACKGROUND OF THE INVENTION

The present invention generally relates to ways of characterizing health related disorders. More particularly, the invention provides a system and method for visualizing information related to the sleep of an organism such as a mammal or human being. But it would be recognized that the invention has a much broader range of applicability such as applicability in situations where body position is a consideration.

Several disorders of sleep are known, including but not limited to snoring, insomnia, restless legs syndrome, upper airway resistance syndrome (UARS), and sleep apnea and its subtypes: obstructive sleep apnea (OSA) and central sleep apnea (CSA). To characterize disorders afflicting patients during sleep, diagnostic tests known as "sleep studies" may be performed. During a typical sleep study, physiological data are collected from the patient by various physiological sensors during a night's sleep. A type of sleep study called polysomnography (PSG) normally collects physiological data from a plurality of data channels over several hours. Belcher (Sleeping: On the Job! 2002, page 138) describes 16 to 18 different data channels for a typical PSG study. The resulting data set may be large. Lipman (Snoring from A to Zzzz. 1998, page 115) reports that a paper record of a PSG study may require one-half mile of paper. Computers and digital data storage have, in many cases, reduced the need for paper in sleep studies, but the quantity of information resulting from a sleep study may still tax the patience of a busy health care professional who wants to rapidly assess the clinical implications of the data.

Efficiently presenting a large data set to a busy health professional can be challenging. Much of the data collected during a sleep study are quantitative. Presenting quantitative data graphically has often proven advantageous. Tufte (The Display of Quantitative Information. 1983, page 9) notes: "Modern data graphics can do much more than simply substitute for small statistical tables. At their best, graphics are instruments for reasoning about quantitative information. Often the most effective way to describe, explore, and summarize a set of numbers —even a very large set—is to look at pictures of those numbers. Furthermore, of all methods for analyzing and communicating statistical information, well-designed data graphics are usually the simplest and at the same time the most powerful."

Well-designed data graphics are, of course, generally advantageous, and Tufte has spent considerable effort teaching the principles of good data graphical design. He believes (Tufte. Supra. Page 13) graphical displays should, among other desiderata:

show the data;
avoid distorting what the data have to say;
present many numbers in a small place;
make large data sets coherent;
encourage the eye to compare different pieces of data;
reveal the data at several levels of detail, from a broad overview to the fine.

Data from sleep studies have been displayed in a plurality of graphical formats, often satisfying Tufte's desiderata only partially.

FIG. 1A shows a segment of raw PSG data rendered graphically (from Undevia et al. Internet document, 2004). At least 17 channels of physiological data are presented, graphed in separate panes on a common horizontal (time) axis, with each pane having its own vertical axis. The top 8 panes represent electroencephalographic channels, with successive panes representing the left oculogram (the "LOC" pane of the graph, as labeled at the left margin), the right oculogram (ROC), chin electromyography (EMG chin), left and right leg electromyography (LAT/RAT), nasal airflow (Airflow), thoracic respiratory movement (Chest), abdominal respiratory movement (Abdomen), electrocardiogram (ECG), and arterial oxygen saturation (SAO2). Tufte advocates graphical designs that "encourage the eye to compare different pieces of data," but the relatively large vertical distance between some channel plots in this figure generally makes inter-channel comparisons less inviting. Approximately 5 minutes of data are presented in FIG. 1A. Because a PSG study may collect data for 8 hours or longer, on the order of 100 such pages may be required to fully present a single study.

FIG. 1B shows approximately 6 hours 43 minutes of four data channels from a PSG study, plotted in four separate panes (from Undevia et al. Supra). From top to bottom the panes plot sleep stage, oxygen saturation, apnea-hypopnea event types, and delivered facemask pressure against time. Some of these data inherently vary slowly, allowing longer periods of time to be plotted in a given space without losing resolution. Plotting certain types of data, e.g. electrocardiogram signals, at the time scale of FIG. 1B would typically be far less informative because such data signals inherently vary faster. Although FIG. 1B needs only one page to plot results from the entire time of a sleep study, it appears to have a lower information density than FIG. 1A. Thus, FIG. 1B may have a potential for application of Tufte's desideratum to "present many numbers in a small place." Another shortcoming of FIG. 1B is, as in FIG. 1A, the relatively large vertical distance between channel panes, making inter-channel comparisons generally less inviting.

In addition to polysomnography, other types of sleep studies may be performed. For example, several types of "reduced sensor" diagnostic devices collect fewer channels of physiological data than typical polysomnography. A certain tension often exists in designing a reduced sensor device between maximizing diagnostic yield and minimizing technical failures. In many cases diagnostic yield increases with the number of sensors used to collect physiological data from a patient being tested with the device. However, in many cases the likelihood of a technical failure during a study also increases with the number of sensors used. Thus, the choice of which sensors to design into a reduced sensor device is often critical. As Douglas (Sleep Med Rev. 2003;7:53-59) remarks: "The choice of sensors to be used is open to considerable debate."

The American Academy of Sleep Medicine provides some guidance about sensor selection. A committee writing on their behalf states "Body position must be documented during recordings to assess the presence of OSA" (Thorpy et al. Sleep. 1994;17:372-377). There is evidence that the severity of OSA in some people varies according to their body position during sleep. In such persons, OSA is typically more severe when the person is lying on their back, as opposed to lying on a side or face down.

If positional data are collected during a sleep study, it is often desirable to visualize these data. FIG. 2 shows a plot 200 of a patient's body position during a night of sleep, as recorded by a reduced sensor device. Time, in minutes, is on the horizontal axis 210, and body position is on the vertical axis 220. Four body positions are recognized by this reduced sensor device, corresponding to being face up, face down, facing left, or facing right, as shown in labeling of vertical axis 220. The plot shows, for example, that initially the patient was facing right for a little more than an hour, then was on his or her back for about the next two hours ("facing up"). This simple plot of position-vs-time may be incorporated into a PSG-style plot by, for example, replacing one of the 17 panes plotted in FIG. 1A or one of the 4 panes plotted in FIG. 1B with the pane plotted in FIG. 2 (and adjusting the time axis as necessary, of course). Such a substitution, however, retains most of the shortcomings present in FIG. 1A and FIG. 1B.

Some reduced sensor devices collect sound as a physiological parameter for use in assessing breathing disorders of sleep, as taught in co-pending U.S. patent application Ser. No. 11/094,911. One factor in the visualization of digitized sound data is the high typical sampling rate, e.g. 2000 samples per second. Thus, in an 8-hour period, over 57 million sound samples may be collected. Although this may be considered a large data set in many visualization applications, there are several examples where signals similar to raw sound are plotted on a common time axis with other physiological signals.

In some cases the envelope of an audio signal may be plotted to give an indication of the loudness of the sound. (Note: we treat sound level, sound intensity, and sound loudness as the same concept herein.) However, the sampling rate of an envelope of an audio signal is often significantly lower than the sampling rate of the signal on which it was based. Thus, the envelope may be plotted similarly to some of the channels in FIG. 1A and FIG. 1B, but with some of the same shortcomings discussed for those figures.

Potsic (Laryngoscope. 1987;97: 1430-1437) (Otolaryngol Head Neck Surg. 1986;94:476-480) teaches a method for representing several minutes of sound data collected by a reduced sensor device. His approach directly represents a quantity related to sound intensity and, indirectly, respiratory regularity. Furthermore, the example plots he provides do not include data from a channel other than sound, which is likely to be a shortcoming of his approach should comparison of sound and other channels be desired.

Other approaches to visualization of sound provide a binary representation of whether sound level (or intensity) have exceeded a certain threshold (Stoohs and Guilleminault. Eur Respir J. 1990;3:823-829) (Penzel et al. Sleep. 1990;13: 175-182) (U.S. Pat. Nos. 4,982,738; 5,275,159; and 6,120,441). While potentially compact, this degree of data reduction may be associated with an undesirable loss of information in some applications.

From the above, it is desirable to have improved techniques for characterizing health related disorders.

BRIEF SUMMARY OF THE INVENTION

A method for improved visualization of information related to the physiology of a sleeping patient is disclosed. Physiological information from the patient is obtained by a device, converted to digital format, and transformed into physiological data of two or more types. Physiological data of two or more types are combined into a compact graphical display representing data from all physiological data types.

In one embodiment sound information comprises a first data type. An envelope of the sound information is displayed against a time axis. Physiological data of a second type is displayed against the same time axis such that variations in the values of the data elements are represented as visually distinguishable variations in the region above the envelope line, e.g. variations in hue, saturation, color, texture, and the like. Physiological data of a third type may be displayed against the same time axis such that variations in the values of the data elements are represented as visually distinguishable variations in the region below the envelope line. Physiological data of a fourth type may be displayed against the same time axis such that variations in the values of the data elements are represented as visually distinguishable variations straddling the envelope line. Additional physiological data may be plotted against the time axis.

Various additional objects, features, and advantages of the present invention can be more fully appreciated with reference to the detailed description and accompanying drawings that follow.

BRIEF DESCRIPTION OF THE DRAWINGS

FIGS. 1A and 1B illustrate a visualization of polysomnographic information.

FIG. 2 illustrates a visualization of body position information.

FIG. 4A2 shows substantially the same information as FIG. 4A, but with a greater range in the scale of the vertical axis.

FIG. 4A3 shows an enlarged view of the lower left corner of

FIG. 4A.

(Color versions of FIGS. 1A, 1B, 4A, and 5 are being supplied on CD-ROM.)

DESCRIPTION OF THE SPECIFIC EMBODIMENT

Figure 3:
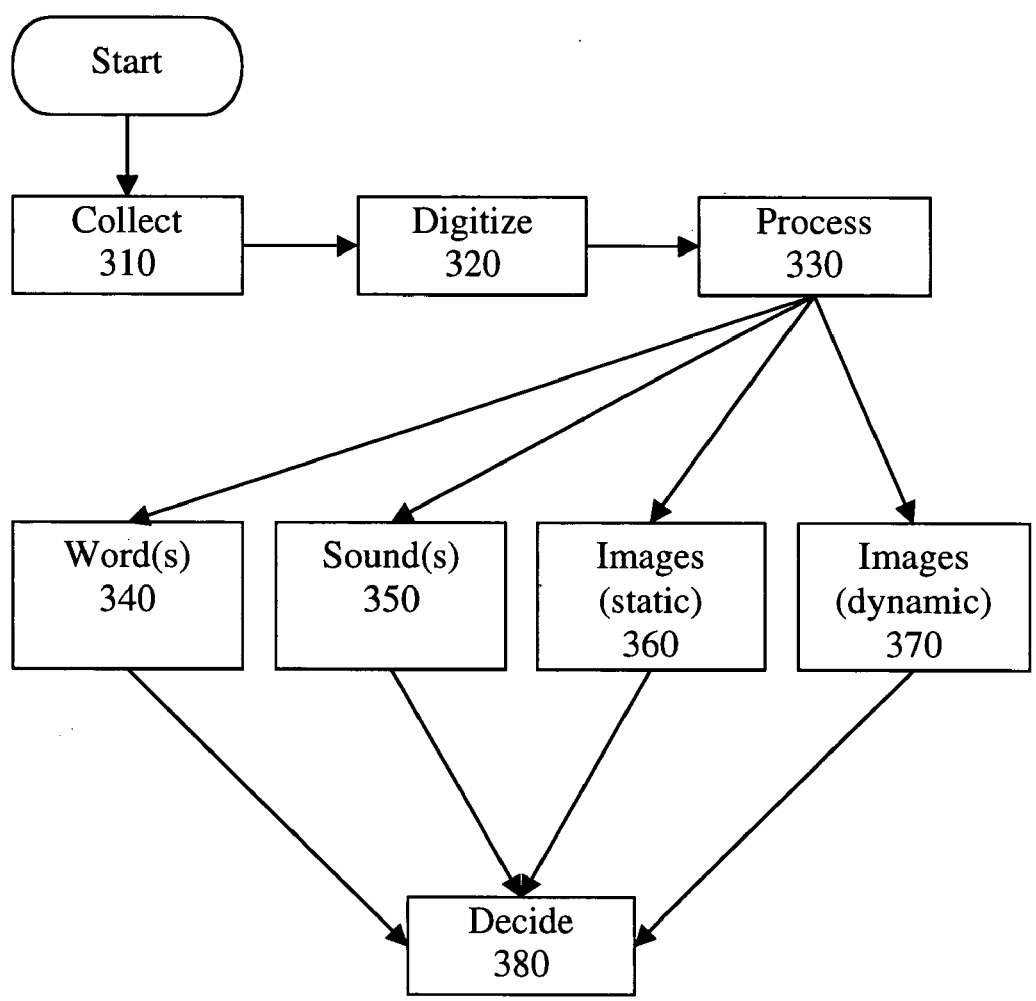
FIG. 3 shows a flowchart of the operation of one embodiment of a system for communicating physiological information.

FIG. 3 shows a flow diagram of steps in communicating physiological information about a human or otherwise mammalian patient. In one method, in data collection step 310 a device may acquire physiological data from a patient who is sleeping (or attempting to sleep). The device may be a polysomnographic device or a reduced sensor device, e.g. as taught in co-pending U.S. patent application Ser. No. 11/094,911. In step 320 the data collected in step 310 may be converted to digital format, e.g. with an analog-to-digital converter.

In one method, optional step 330 may result in one or more processing transformations being applied to the digitized data provided from step 320. For example, audio data may be filtered, unusable portions of data may be identified and tagged, artifacts in the data may be removed, diagnoses may be made, and algorithmic transformations may be applied to the data. An example of an algorithmic transformation is computation of an envelope of an audio signal. Merely by way of example, processing step 330 may occur in a digital computer.

Information about the data collected in step 310 or about the data created in step 330 may be represented in one or more forms. In one method, words may be generated in step 340, e.g. "The mean heart rate during the study was 79 beats per minute." In another method, sounds may be created in step 350, e.g. playing back tracheal sounds recorded from the patient between 2:06 a.m. and 2:07 a.m. In yet another method, one or more static images may be generated in step 360. Used in this sense, "static" means "unchanging." In one method, an animation or moving picture may be created in step 370, generated, for example, from a plurality of static images.

In one embodiment, one or more of steps 340, 350, 360, and 370 may be combined. For example, sound from step 350 may be combined with an animation from step 370. As an additional example, words from step 340 may be used to caption an image resulting from step 360. As another example, a static image (from step 360) representing one minute of an envelope signal may be combined with an animation of a vertical bar taking one minute to sweep across the static image (from step 370), and these may be combined with the sound of the patient's breathing (from step 350) synchronized to the position of the bar with respect to the static envelope image. In this example, words (from step 340) may appear and disappear, e.g. the word "apnea" may appear when the bar begins to sweep across a period of time associated with an apnea.

In one method, the information from one or more of steps 340, 350, 360, and 370 is received by a decision-maker, who uses all or some of the information to make a decision about the diagnosis and/or management of the patient.

We have discovered that certain types of static images, as may result from step 360, may facilitate decision making in step 380.

Figure 4A:
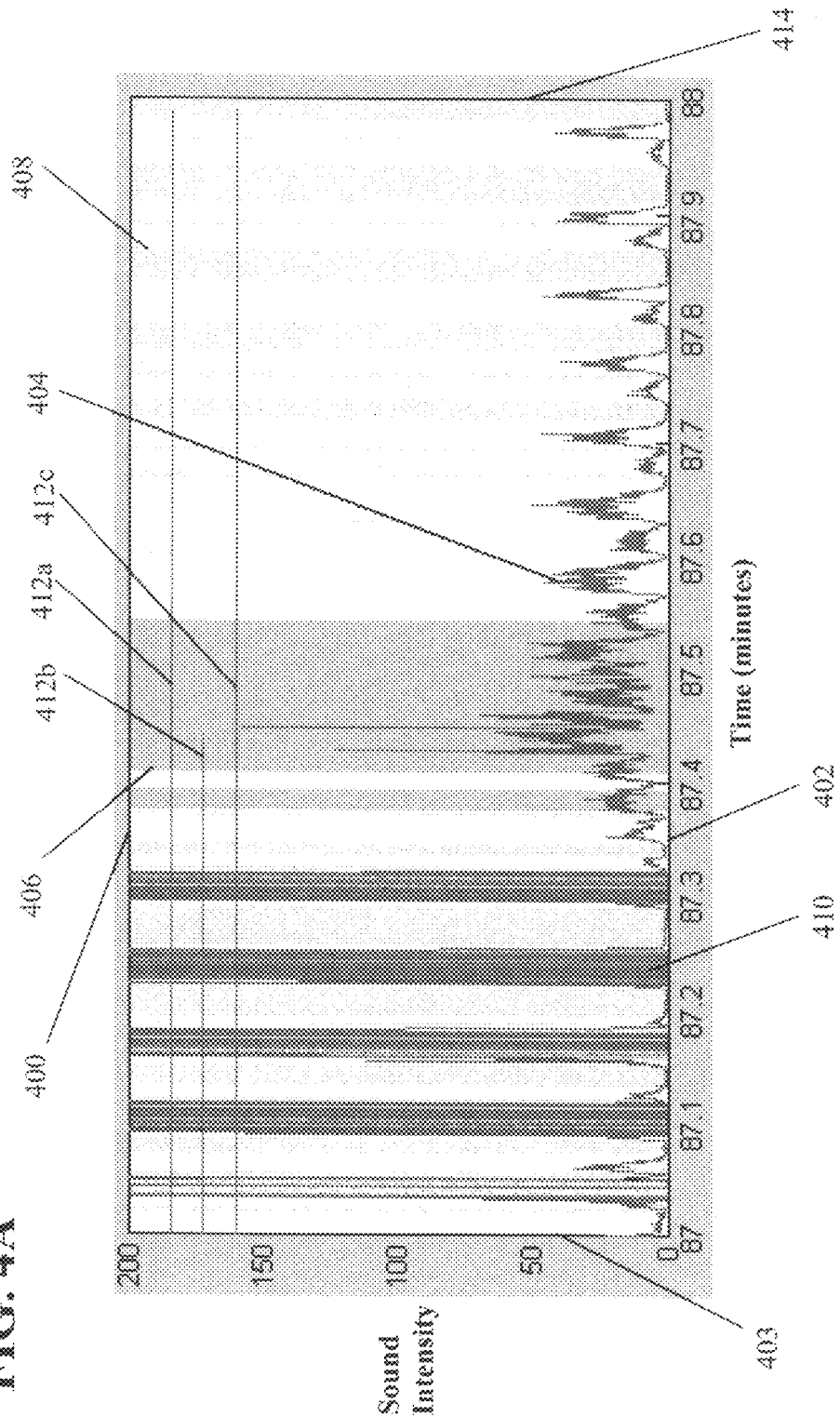
FIG. 4A shows an embodiment of a plot of five physiological parameters.

FIG. 4A illustrates an embodiment in which values of five different physiological parameters are represented graphically in one graphical pane 400. FIGS. 4A2 and 4A3 provide alternate views into FIG. 4A. (FIG. 4A3 is an enlargement of the lower left corner of FIG. 4A, while FIG. 4A3 replots substantially the same data as FIG. 4A but with an enlarged scale on the vertical axis) In FIG. 4A the parameters derived from data collected (as in step 310) during one minute of a sleep study of a patient. In one embodiment the data may have been collected from a plurality of sensors including, but not limited to, a tracheal microphone, an accelerometer coupled to the patient's wrist, and a body-position sensor. In graphical pane 400, the five parameters are plotted against a common time axis 402, as follows:

1. A jagged dark blue line 404, sometimes known as an "envelope trace," may represent the envelope of sound recorded during the one minute of time indicated by horizontal axis 402 for this study. In FIG. 4A sound level increases from bottom to top on the vertical axis 403. Breaths, in one embodiment, are normally identifiable in envelope trace 404 as a mountain-like rise and fall. (Some breaths appear as double mountains because inhalation and exhalation appear as separate peaks.) In FIG. 4A and in FIG. 4A2, for example, there are 6 complete breaths represented to the right of the peak indicated by the item 404 pointer. The loudness of the first five breaths in FIG. 4A have been capped at 200 units, and at 2400 units in FIG. 4A2.

2. The temporal extent of a solidly light-blue-colored "movement" rectangle 406 extending the full height of pane 400 may represent a period of time during which the patient moved his or her wrist;

3. The temporal extent of a solidly yellow-colored "apnea" area 408 above envelope trace 404 may represent a period of time during which little or no sound intensity above a baseline was present in the sound envelope. In one embodiment the lower border of an apnea area 408 is generally a portion of the envelope trace 404.

4. The temporal extent of a solidly red-colored "snoring" area 410 below envelope trace 404 may represent a period of time during which the patient snored. In one embodiment the upper border of a snoring area 410 is generally a portion of the envelope trace 404. FIGS. 4A2 and 4A3 also illustrate this embodiment. FIGS. 4A, 4A2, and 4A3 show four clear snoring breaths from 87.1 minutes to 87.3 minutes.

5. One or more horizontal lines 412a, 412b, 412c near the top of pane 400 may represent the position of the patient's body (with respect to earth's gravity) at various times during the minute represented by horizontal axis 402.

(Note: We frequently use the numbers for areas 406, 408, and 410 to refer to the generic class of each of these area types.)

In one embodiment, apnea area 408 may be considered to represent a period in which little air flowed in the patient's trachea. Because airflow in a trachea generally produces sound detectable by a suitable tracheal microphone, the absence (or near-absence) of a signal from such a microphone is often an indication of the absence (or near-absence) of tracheal airflow. FIG. 4A displays several short periods of apnea, e.g. between end-exhalation-and start-inhalation from minutes 87.7 to 88. We call such periods "micro-apneas" because of their short duration (e.g. one second or less) as compared to the common requirement of 10 seconds of apnea in the diagnosis of obstructive sleep apnea.

For convenience we refer to this visualization of Position, Snoring, Apnea, Loudness (envelope), and Movement as the PSALM graph. However, because other embodiments may plot different parameters, use of the PSALM acronym should not be interpreted as limiting.

In one embodiment, the colors of movement area 406, apnea area 408, and snoring area 410 may all be different, such that they may be readily distinguished. In another embodiment, areas 406, 408, and 410 may have the same color, but have different texture patterns, e.g. cross-hatching, dots, and the like, to distinguish them.

In one embodiment the representation of a wrist movement by a movement rectangle 406 may remove from view representations of a low sound level (apnea area 408) or snoring (area 410) occurring during the same time period as the wrist movement. The phrases "movement trumps snoring" and "movement trumps apnea" may be used to describe these interactions. These interactions are often acceptable, because if a patient is moving it is generally true he or she is awake during the period of movement, and thus there is relatively less concern about whether the patient is then snoring or making little sound. Generally, the envelope trace 404 will be visible as a line appearing to lie above (in the z-axis) the solidly colored movement rectangle 406.

In one embodiment, sound epochs may be rated according to their degree of resemblance to a snoring definition, a measure we call "snoringness." In an embodiment snoringness may be graphically represented by varying the saturation or other characteristic of the color of snoring area 410. For example, a deep red color may indicate a sound that is typical for a snore, while a light red color may indicate that a sound is atypical, but not entirely unlike, a snore. In such an embodiment lack of snoringness may be represented without a color. In another embodiment, varying snoring loudness may be represented by varying the color of snoring area 410, but this is not often preferred, as the vertical extent of envelope trace 404 also represents sound loudness.

In another embodiment the horizontal lines 412 representing body position may do so according to a code. For example, the presence of three lines (412a, 412b, 412c) at a specific time may indicate the patient, while lying in bed., was facing upwards at that time. The presence of one line (412a) may indicate the patient is facing down, and the presence of two lines may indicate the patient is on his or her side (412a and 412c for facing left, and 412b and 412c for facing right). Applying this code to FIG. 4A discloses that the patient was on his or her back for approximately the first 0.44 minutes, before assuming a left-facing position.

In another embodiment body position may be represented by icons arrayed in a horizontal line near the top of pane 400, such that an icon plotted at a time t (per horizontal axis 402) would represent the patient's body position in bed at that time t. In one embodiment the icons are arrowheads facing up, down, left, and right with respect to pane 400, representing, respectively, the patient facing up, down, left, and right.

The technique of representing body position in a vertically small extent, as shown, for example, in FIG. 4A, may potentially be applied to any graph in which the representation of body position is desired. In one embodiment a body position datum may assume relatively few values, e.g. up, down, left, right, facilitating the use of coding approaches, as above. Sleep/wake stage is another physiological variable that in some embodiments can assume relatively few values, e.g. wakefulness, rapid eye movement (REM) sleep, and stages one, two, three, and four sleep. As a result of this similarity between body position and sleep/wake stage, in one embodiment sleep/wake stage may be amenable to one or more of the visualization techniques applied to body position.

In another embodiment one or more additional parameters may be plotted on pane 400 as one or more traces extending from left to right, preferably distinguishable from each other by color, thickness, dashing, and the like. Oxygen saturation, for example, could be plotted as a series of line segments, with numerical labeling on the right vertical axis 414 to assist in discerning the numeric values indicated by the oximetry trace. In such an embodiment it may be preferable to omit horizontal lines 412a through 412c, as the plot may become too crowded in appearance. In another embodiment, a representation of body position may be displayed in a small vertical extent just above the top border of pane 400. In general, however, different plotting elements and physiological parameters may be included or not included in various embodiments according to the type of decisions a graph is meant to support.

A representation of data such as that illustrated in FIG. 4A may be advantageous in an embodiment because it may reduce five (or potentially more) channels of data into one graphical pane, thereby conserving vertical extent, keeping related data together and, in the words of Tufte (supra.), encouraging "the eye to compare different pieces of data." We have discovered, for example, that plotting 8 lines of 2 minutes each on standard copier paper with an inkjet printer will, in many cases, retain sufficient resolution for most uses. We have also discovered that printing two pages on one side of one sheet of standard copier paper also retains adequate resolution in many cases. Thus, one embodiment may print 32 minutes of data on each side of a piece of paper, meaning that only about 8 pieces of paper would be required to fully visualize the PSALM data obtained in an 8-hour sleep study.

In some embodiments it is preferable to use a pale color for apnea area 408 because the breathing of some persons includes a high percentage of micro-apneas, leading to an almost solidly colored plot that can wash out certain other plotted elements. In another embodiment the color saturation or other characteristic of apnea area 408 may depend on the proportion of nearby time that is apneic, with the saturation increasing as the amount of local apnea increases.

A representation of data such as that illustrated in FIG. 4A may be advantageous in an embodiment because of certain patterns that might be produced by the representation. For example, rhythmically regular snoring may be very apparent when looking at a PSALM plot displaying several minutes of envelope traces 404 and corresponding snoring areas 410. This phenomenon may be advantageous given that Smolley and Bruce (The Snoring Cure. 1999, page 167) remark: "Snoring that is regular—without interruptions [of various types]—is not likely to represent a serious problem." Similarly, in some cases irregular snoring is easy to discern by inspecting a PSALM plot.

In one embodiment choosing an emotionally-laden color for snoring area 410 may be advantageous because some people attach an emotion to snoring problems and because dense snoring (i.e. snoring with almost every breath) may result in a PSALM plot rather suffused with the snoring area 410 color. Thus, red, with its usual active overtones, may be an appropriate color for an embodiment if complaints of snoring are provoking discord between two people.

Figure 4B:
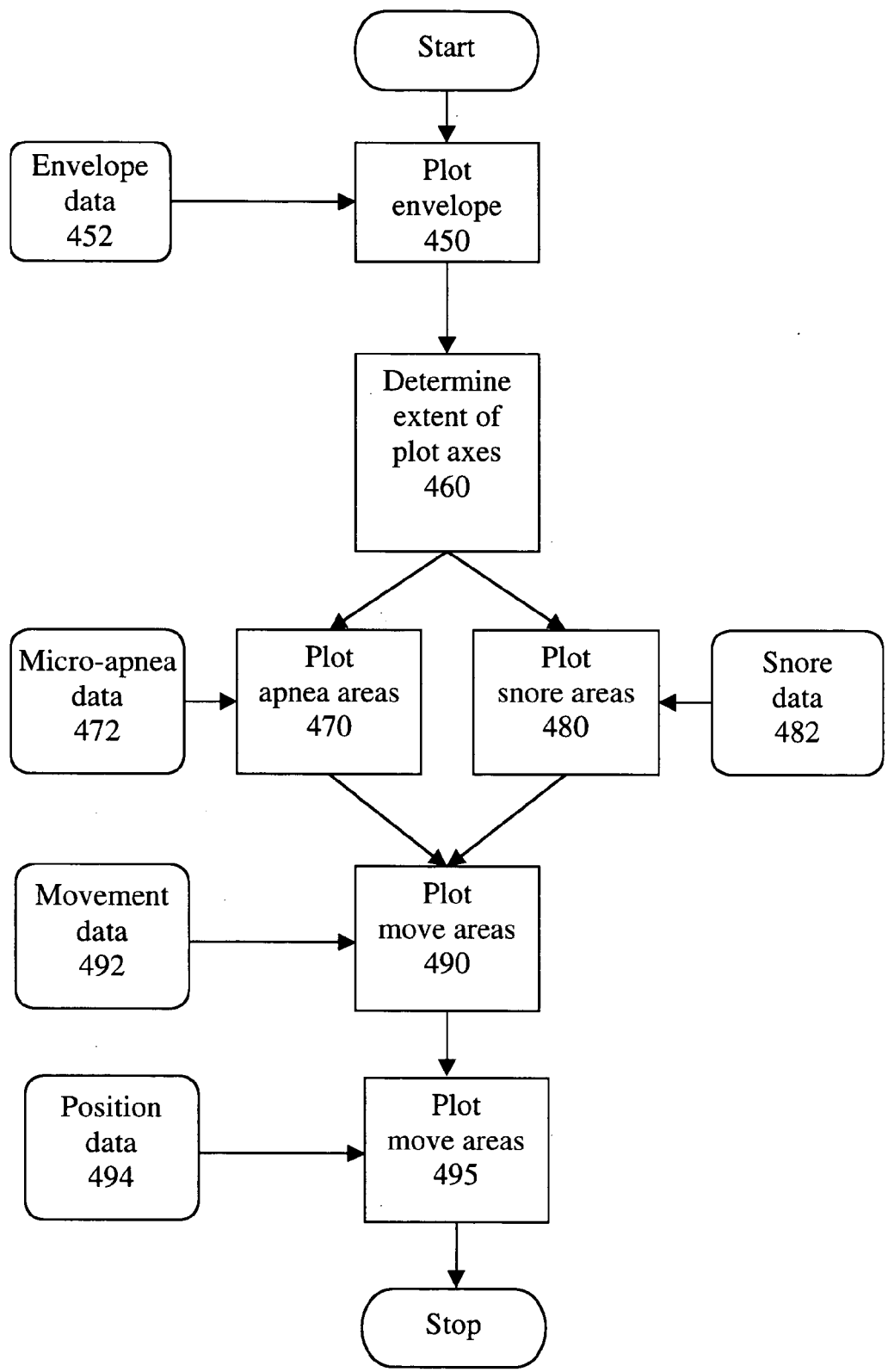
FIG. 4B shows a flowchart of the operation to produce FIG. 4A.

In one method, the graph of FIG. 4A may be generated according to FIG. 4B. Data 452 defining the envelope may be used to plot the envelope trace 404 (step 450). After such a plot, the axes of the plot may have a defined extent that can be read (step 460). Using the data 472 defining apnea periods (whether micro- or macro-), the apnea area 408 may be plotted (step 470). Some graphical software routines may facilitate this step by using envelope data 452 and the top boundary of the vertical plot axis to define a polygon that can be plotted and filled with a color as a single function call. Similarly, the data 482 defining periods of snoring may be used to plot snore areas 410 (step 480). The data 492 defining limb movement may then be used to plot move areas 406 (step 490) and the position data (494) may be used to plot the horizontal position lines 412 (step 495). In some cases, envelope trace 404 will need to be replotted (not shown) after one or more of the other drawing steps have occurred.

Figure 5:
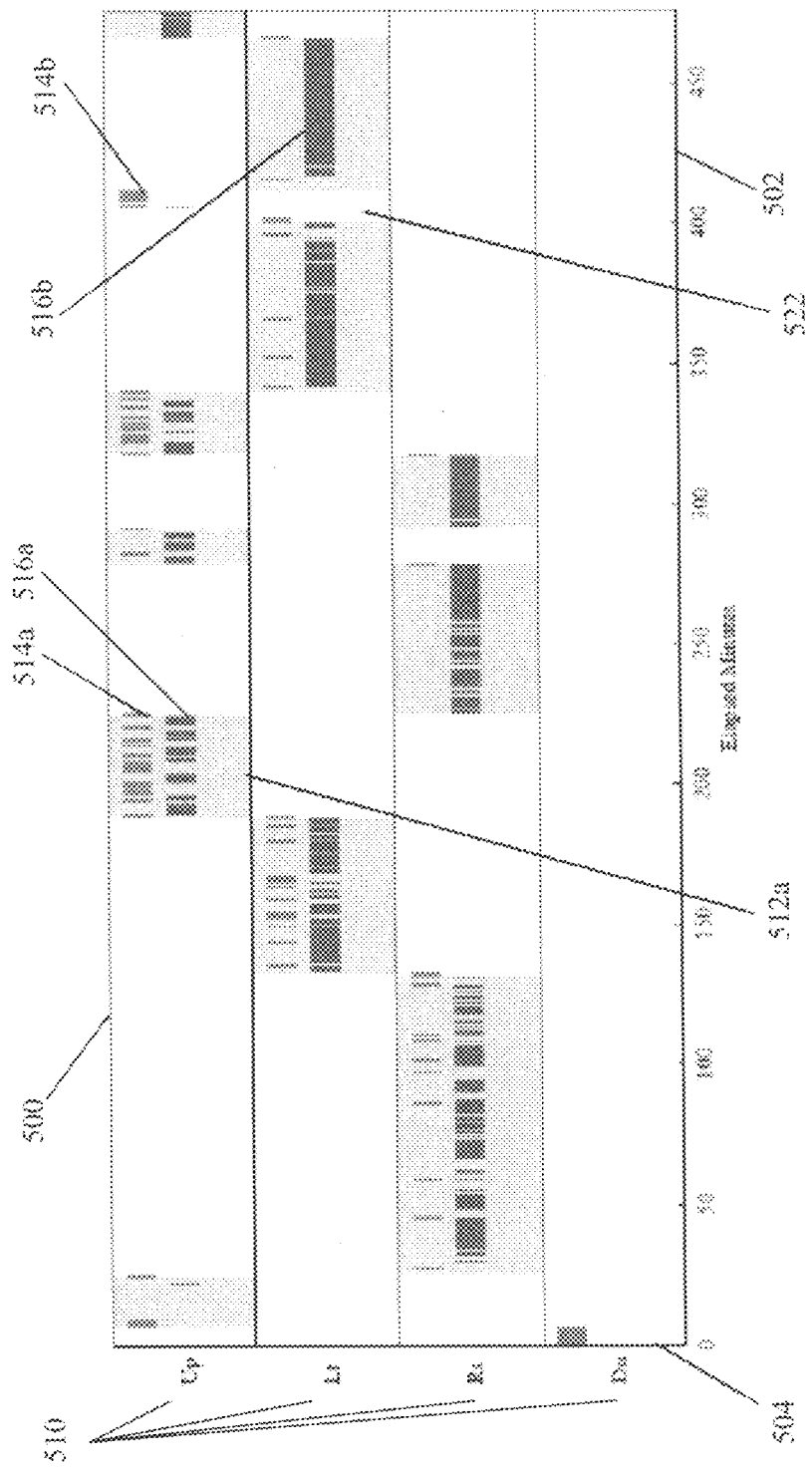
FIG. 5 shows an embodiment of a plot of position and three additional parameters.

FIG. 5 shows one embodiment of a graphical plot in a single pane 500 relating body position to three other variables: snoring, wrist movement, and time. Time may run across a horizontal axis 502. A vertical axis 504 may specify four (or some other number of) body positions 510. The extent of the vertical axis may be divided with horizontal lines into four strata, one for each body position. Certain rectangular portions of some strata may be shaded (e.g. 512a) with a color, signifying that the patient had assumed the corresponding body position at the time encompassed by the horizontal extent of the rectangular color shading. Shaded areas (e.g. 512a) may contain one or more sub-strata 514a and 516a possibly including event indicators. A first sub-stratum 514 may display a vertical mark during times associated with an arm movement of the patient. A second sub-stratum 516 may display a vertical mark during times associated with a snore. In some embodiments a third sub-stratum (not shown) may display a vertical mark during times associated with an oxygen desaturation, based on data from an oximeter. In another embodiment other parameter(s) may be displayed in various sub-strata, e.g. apnea and hypopnea events, respiratory effort related arousals, and the like. In one embodiment each sub-stratum has its own vertical axis, which may allow continuous variables to be represented.

In one embodiment event markers for different subs-strata are distinguishable, e.g. by color or by texture. In another embodiment, a color assigned to a class of event marker has mnemonic value, e.g. red is assigned to a blood-related event such as oxygen desaturation.

In one embodiment, graphical contents of pane 500 may be rendered in the Postscript language (Adobe Corporation, San Jose, Calif.). A potential advantage of rendering in Postscript is that a plurality of magnifications can be applied to pane 500, using, for example, the magnification capabilities provided by Adobe Acrobat Reader software. A result is that a sub-stratum 516*b*, which appears at low magnification to have event markers in a relatively long and unbroken extent in time may, at high resolution, resolve into separate and distinguishable snoring events.

Another potential advantage of the graphical display technique illustrated in FIG. 5 is that it may have the potential to convey intuitively a correlation between body position and events in sub-strata (e.g. 514 and 516). For example, inspection of sub-stratum 516 across the entire study in FIG. 5 seems to disclose that snoring is present in all body positions to an approximately equal degree, as the density of snoring marks appears approximately the same in all strata 510. Inspection of sub-stratum 514, however, seems to suggest that arm movement was more common in this study when the patient was facing up (i.e. on his or her back), as the density of arm movement event marks appears greater in the time periods of the "Up" stratum.

An additional potential advantage of the graphical display technique illustrated in FIG. 5 is that it may convey the body positions the patient assumed during the sleep study. Gaps in shading of the strata 522 may indicate the system was unable to assign a body position for the corresponding period of time, and as a result event markers 514*b* are sometimes plotted outside of a shaded stratum.

Figure 6A:
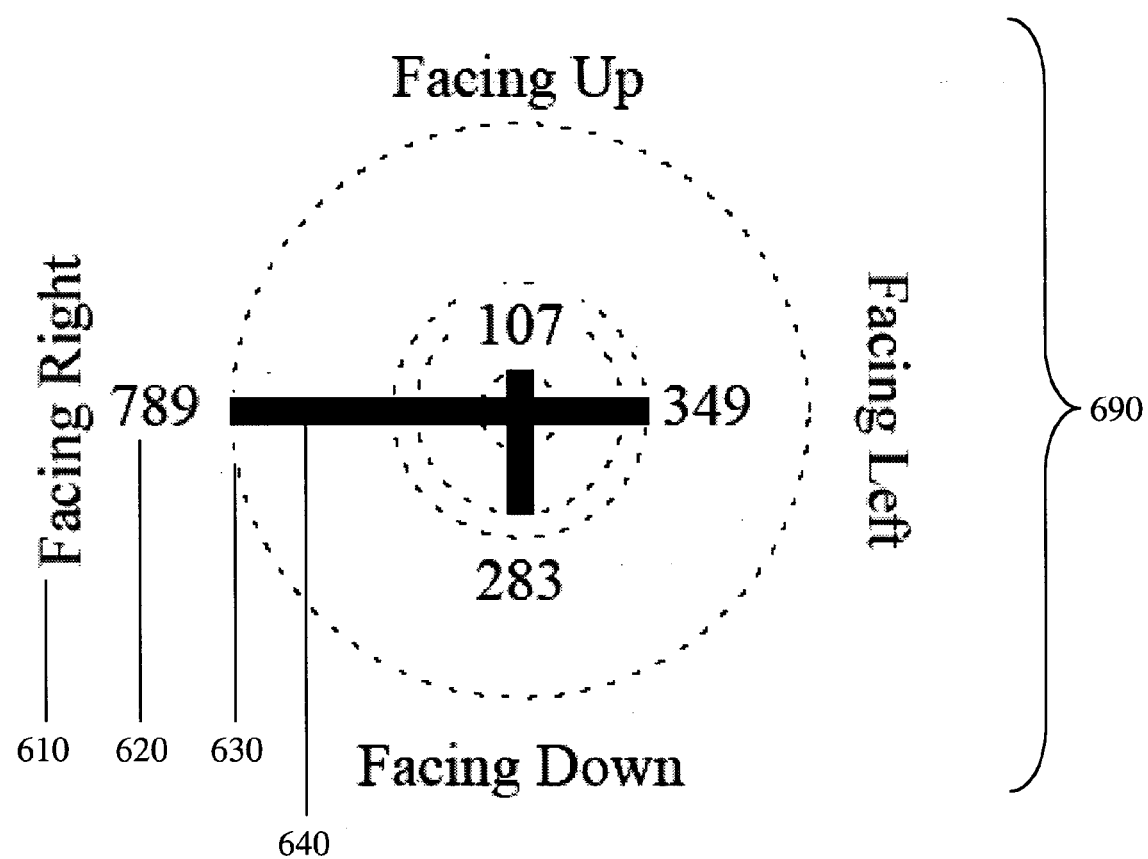
FIG. 6A shows an embodiment of a positional histogram.

FIG. 6A shows one embodiment of a "positional histogram" 690. A positonal histogram may plot a quantity for each of the canonical body positions in an embodiment and may further provide various ways to compare the quantities between positions. FIG. 6A shows a positional histogram 690 with 4 canonical positions (facing right, facing left, facing down, and facing up). The general appearance of the plot may be that of a circle with foreshortened spokes. When there are 4 canonical positions, each body position may be allocated one quarter of the circle. Thus, each of the canonical positions in FIG. 6A is allocated a quadrant. It may be advantageous to allocate the quadrants (or other sectors) so as to provide a mnemonic correlation between the figure and the actual orientation of the positions. Thus, in FIG. 6A, for example, the quadrant allocated to the "facing up" position is at the top of the figure.

We will temporarily focus our discussion of FIG. 6A on the "facing right" quadrant. Each position's sector may include, but is not limited to, a caption 610, a quantity label 620, a histogram bar 640, and a comparison circle 630. Caption 610 may generally be a word or two that explains which position is displayed. Quantity label 620 may generally be a number corresponding to the value of the graph's parameter for the given position. Histogram bar 640 may be akin to the bars on a standard histogram, but with a different orientation, i.e. oriented in the same direction as the quadrant of the corresponding body position. Comparison circle 630 may be defined by two points: the center of FIG. 6A and the tip of a histogram bar 640. All histogram bars meet in the center of FIG. 6A. Comparison circle 630 reinforces the distance from the center of FIG. 6A to the top of histogram bar 640 for a given section. Comparison circle 630 may be used to make quick graphical "greater than" and "less than" comparisons between positions, as the circle extends into all quadrants, allowing a rapid comparison with the histogram bars in other quadrants.

Figure 6B:
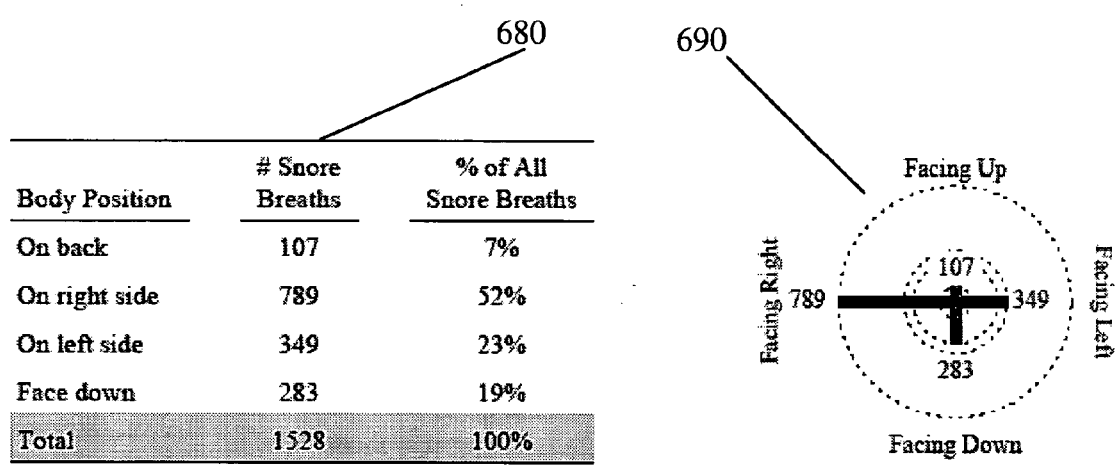
FIG. 6B shows an embodiment of a positional histogram teamed with a table.

In one embodiment a positional histogram plot 690 may be paired with a table 680 reporting positional data, as in FIG. 6B. Table 680 and positional histogram 690, for example, both may report the number of snoring breaths, and the proportion of snoring breaths, occurring in each of the canonical body positions. This may be advantageous in the case of persons who are weak readers and are more visually oriented.

It is seen that certain visualization techniques may improve the quality of information display, according to some of the criteria enunciated by Tufte. Although the application of such techniques herein has been related to sleep physiology, the techniques are not limited to sleep physiology.

It should be noted that the above sequence of steps is merely illustrative. The steps can be performed using computer software or hardware or a combination of hardware and software. Any of the above steps can also be separated or be combined, depending upon the embodiment. In some cases, the steps can also be changed in order without limiting the scope of the invention claimed herein. One of ordinary skill in the art would recognize many other variations, modifications, and alternatives. It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for transforming sound information into a visual representation of the breathing of a patient comprising:

identifying a first set of physiological data values derived from respiratory sound information collected from the patient during a time interval associated with a sleep period of the patient;

using a computer, obtaining from the first set of physiological data values an envelope signal, the envelope signal being indicative of a loudness, level, or intensity of the respiratory sound;

outputting within a spatial region having a first axis and a second axis an envelope trace derived from the envelope signal, with the time interval associated with the sleep period represented on the first axis and the magnitude of the envelope signal represented on the second axis; and outputting within the spatial region provided by the first axis and the second axis a first plurality of graphical components, each of the first plurality of graphical components being associated with a different time period provided on the first axis, at least one of the first plurality of graphical components representing a degree of snoring during the time period associated with the graphical component by the use of a color or texture pattern of the graphical component, wherein at least three different degrees of snoring, one of which degrees of snoring may be the absence of snoring, are represented among the first plurality of graphical components; and each of the first plurality of graphical components having a top border conforming to the envelope trace.

2. The method of claim 1 wherein the duration of the time period associated with each graphical component in the first plurality of graphical components is less than or equal to the duration of an inhalation by the patient.

3. The method of claim 1 wherein the duration of the time period associated with a graphical component in the first plurality of graphical components is less than or equal to one second.

4. A method for transforming sound information into a visual representation of the breathing of a patient comprising:
identifying a first set of physiological data values derived from respiratory sound information collected from the patient during a time interval associated with a sleep period of the patient;
using a computer, obtaining from the first set of physiological data values an envelope signal, the envelope signal being indicative of a loudness, level, or intensity of the respiratory sound;
outputting within a spatial region having a first axis and a second axis an envelope trace derived from the envelope signal, with the time interval associated with the sleep period represented on the first axis and the magnitude of the envelope signal represented on the second axis;
outputting within the spatial region provided by the first axis and the second axis a first plurality of graphical components, each of the first plurality of graphical components being associated with a different time period provided on the first axis, at least one of the first plurality of graphical components representing a degree of snoring during the time period associated with the graphical component by the use of a color or texture pattern of the graphical component; and each of the first plurality of graphical components having a top border conforming to the envelope trace; and
outputting within the spatial region provided by the first axis and the second axis a second plurality of graphical components, each of the second plurality of graphical components being associated with a different time period provided on the first axis, at least one of the second plurality of graphical components representing a limb movement by the patient during the time period associated with the graphical component; and each of the second plurality of graphical components having a substantially rectangular shape, with side borders perpendicular to the first axis, a top border parallel to the first axis, and a bottom border parallel to the first axis.

5. The method of claim 4 wherein the top border of each of the second plurality of graphical components is substantially at the maximum extent of the second axis, and the bottom border of each of the second plurality of graphical components is substantially at the minimum extent of the second axis.

6. The method of claim 4 further comprising outputting within the spatial region provided by the first axis and second axis a third plurality of graphical components, each of the third plurality of graphical components being associated with a different time period provided on the first axis, at least one of the third plurality of graphical components representing a body position of the patient during the time period associated with the graphical component; and each of the third plurality of graphical components having substantially linear sub-components parallel to the first axis and positioned substantially between the maximum extent of the second axis and the minimum extent of the second axis.

7. The method of claim 6 further comprising outputting within the spatial region provided by the first axis and second axis a fourth plurality of graphical components, each of the fourth plurality of graphical components being associated with a different time period on the first axis, at least one of the fourth plurality of graphical components representing respiratory airflow of the patient during the time period associated with the graphical component; and each of the fourth plurality of graphical components having a top border that is parallel to the first axis, side borders that are perpendicular to the first axis, and a bottom border that conforms to the envelope trace or is substantially at the minimum extent of the second axis.

8. The method of claim 1 further comprising outputting within the spatial region provided by the first axis and the second axis a second plurality of graphical components, each of the second plurality of graphical components being associated with a different time period provided on the first axis, and each of the second plurality of graphical components being indicative of a value of a physiological parameter during the time period associated with the graphical component, the physiological parameter being selected from blood oxygen saturation, body position, limb movement, and airflow.

9. A computer readable medium having embodied thereon a program, the program being executable by a processor for performing a method for characterizing a state of a patient, the method comprising:
outputting within a spatial region having a first axis and a second axis an envelope trace of respiratory sound associated with the patient during a time interval associated with a sleep period of the patient represented on the first axis, the envelope trace being indicative of a loudness, level, or intensity of the respiratory sound; and
outputting within the spatial region provided by the first axis and the second axis a first plurality of graphical components, each of the first plurality of graphical components being associated with a different time period provided on the first axis, at least one of the first plurality of graphical components representing a degree of snoring during the time period associated with the graphical component by the use of a color or texture pattern of the graphical component; and each of the first plurality of graphical components having a top border conforming to the envelope trace.

10. The computer readable medium of claim 9 wherein the method further comprises outputting within the spatial region provided by the first axis and the second axis a second plurality of graphical components, each of the second plurality of graphical components being associated with a different time period provided on the first axis, at least one of the second plurality of graphical components representing a limb movement by the patient during the time period associated with the graphical component; and each of the second plurality of graphical components having a substantially rectangular shape, with side borders perpendicular to the first axis, a top border parallel to the first axis, and a bottom border parallel to the first axis.

11. The computer readable medium of claim 10 wherein the method further comprises outputting within the spatial region provided by the first axis and second axis a third plurality of graphical components, each of the third plurality of graphical components being associated with a different time period provided on the first axis, at least one of the third plurality of graphical components representing a body position of the patient during the time period associated with the graphical component; and
each of the third plurality of graphical components having substantially linear sub-components parallel to the first axis and positioned substantially between the maximum extent of the second axis and the minimum extent of the second axis.

12. The computer readable medium of claim 9 wherein the method further comprises outputting within the spatial region provided by the first axis and the second axis a second plurality of graphical components, each of the second plurality of graphical components being associated with a different time period provided on the first axis, and each of the second plurality of graphical components being indicative of a value of a physiological parameter during the time period associated with the graphical component, the physiological parameter being selected from blood oxygen saturation, body position, limb movement, and airflow.

* * * * *